United States Patent
Patton et al.

[11] Patent Number: 6,138,668
[45] Date of Patent: Oct. 31, 2000

[54] METHOD AND DEVICE FOR DELIVERING AEROSOLIZED MEDICAMENTS

[75] Inventors: John S. Patton, San Carlos; Robert M. Platz, Half Moon Bay, both of Calif.

[73] Assignee: Inhale Therpeutic Systems, San Carlos, Calif.

[21] Appl. No.: 08/979,024

[22] Filed: Nov. 26, 1997

Related U.S. Application Data

[63] Continuation of application No. 08/576,885, Dec. 22, 1995, Pat. No. 5,775,320, which is a continuation of application No. 08/313,707, Sep. 27, 1994, abandoned, which is a continuation of application No. 07/910,048, Jul. 8, 1992, Pat. No. 5,458,135, which is a continuation-in-part of application No. 07/724,915, Jul. 2, 1991, abandoned.

[51] Int. Cl.$^7$ .................................................. A61M 11/00
[52] U.S. Cl. ................................ 128/200.14; 128/203.12
[58] Field of Search ........................... 128/200.14, 200.23, 128/203.12, 204.23

[56] References Cited

U.S. PATENT DOCUMENTS

| | | | |
|---|---|---|---|
| 2,598,525 | 5/1952 | Fox | 128/203.15 |
| 3,362,405 | 1/1968 | Hazel | 128/203.15 |
| 3,812,854 | 5/1974 | Michaels et al. | 128/200.16 |
| 3,964,483 | 6/1976 | Mathes | 128/203.15 |
| 3,991,304 | 11/1976 | Hillsman | 600/529 |
| 4,036,223 | 7/1977 | Obert | 128/203.15 |
| 4,098,273 | 7/1978 | Glenn | 128/203.21 |
| 4,253,468 | 3/1981 | Lehmbeck | 600/534 |
| 4,452,239 | 6/1984 | Malem | 128/203.15 |
| 4,484,577 | 11/1984 | Sackner et al. | 128/203.28 |
| 4,534,343 | 8/1985 | Nowacki et al. | 128/203.15 |
| 4,624,251 | 11/1986 | Miller | 128/200.14 |
| 4,649,911 | 3/1987 | Knight et al. | 128/200.21 |
| 4,677,975 | 7/1987 | Edgar et al. | 128/200.14 |
| 4,739,754 | 4/1988 | Shaner | 128/203.15 |
| 4,790,305 | 12/1988 | Zoltan et al. | 128/200.23 |
| 4,819,629 | 4/1989 | Jonson | 128/200.14 |
| 4,823,784 | 4/1989 | Bordoni et al. | 128/200.14 |
| 4,907,583 | 3/1990 | Wetterlin et al. | 128/203.15 |

(List continued on next page.)

FOREIGN PATENT DOCUMENTS

| | | |
|---|---|---|
| 53288/90 | 10/1990 | Australia . |
| 60084/90 | 2/1991 | Australia . |
| 9007351 | 7/1990 | Denmark ........................ 128/203.15 |
| 0237507 | 9/1987 | European Pat. Off. . |
| 0347779 | 12/1989 | European Pat. Off. . |
| 0506293 | 9/1992 | European Pat. Off. .......... 128/203.15 |
| 2257351 | 8/1975 | France . |
| WO 90/07351 | 7/1990 | WIPO .............................. 128/203.15 |
| WO 90/15635 | 12/1990 | WIPO . |
| WO 92/10229 | 6/1992 | WIPO . |

OTHER PUBLICATIONS

Elliott et al., "Parenteral Absorption of Insulin From The Lung In Diabetic Children", *Aust. Paediatr. J.*, 23(5):293–297 (1987).

*Primary Examiner*—Aaron J. Lewis
*Attorney, Agent, or Firm*—Townsend and Townsend and Crew LLP

[57] ABSTRACT

A device for accurately delivering aerosolized doses of a medicament disperses a measured amount of drug in a measured volume of carrier gas and transfers the resulting aerosol to a chamber prior to inhalation by a patient. The chamber is filled efficiently with the aerosol, and inhalation by the patient draws the aerosol dose into the lungs. This is followed by the inhalation of atmospheric air that will push the initial dose well into the lung interiors. The apparatus optimally includes a dose regulator, a counter, a clock, a dose memory and a signal to indicate when a dose is ready for inhalation. Optimal chamber designs are disclosed.

10 Claims, 8 Drawing Sheets

U.S. PATENT DOCUMENTS

| | | | |
|---|---|---|---|
| 4,926,852 | 5/1990 | Zoltan et al. | 128/200.23 |
| 4,942,544 | 7/1990 | McIntosh et al. | 364/569 |
| 4,984,158 | 1/1991 | Hillsman | 128/200.14 |
| 5,020,527 | 6/1991 | Dessertine | 128/200.23 |
| 5,027,806 | 7/1991 | Zoltan et al. | 128/200.23 |
| 5,033,463 | 7/1991 | Cocozza | 128/203.15 |
| 5,099,833 | 3/1992 | Michaels | 128/200.14 |
| 5,113,855 | 5/1992 | Newhouse | 128/203.15 |
| 5,161,524 | 11/1992 | Evans | 128/203.15 |
| 5,186,164 | 2/1993 | Raghuprasad | 128/203.15 |
| 5,284,133 | 2/1994 | Burns et al. | 128/200.23 |
| 5,295,479 | 3/1994 | Lankinen | 128/203.15 |
| 5,309,900 | 5/1994 | Knoch et al. | 128/200.14 |
| 5,320,714 | 6/1994 | Brendel | 128/203.15 |
| 5,331,953 | 7/1994 | Andersson et al. | 128/200.23 |
| 5,363,842 | 11/1994 | Mishelevich et al. | 128/200.23 |
| 5,404,871 | 4/1995 | Goodman et al. | 128/200.14 |
| 5,458,135 | 10/1995 | Patton et al. | 128/200.14 |
| 5,775,320 | 7/1998 | Patton et al. | 128/200.14 |

FIG_7
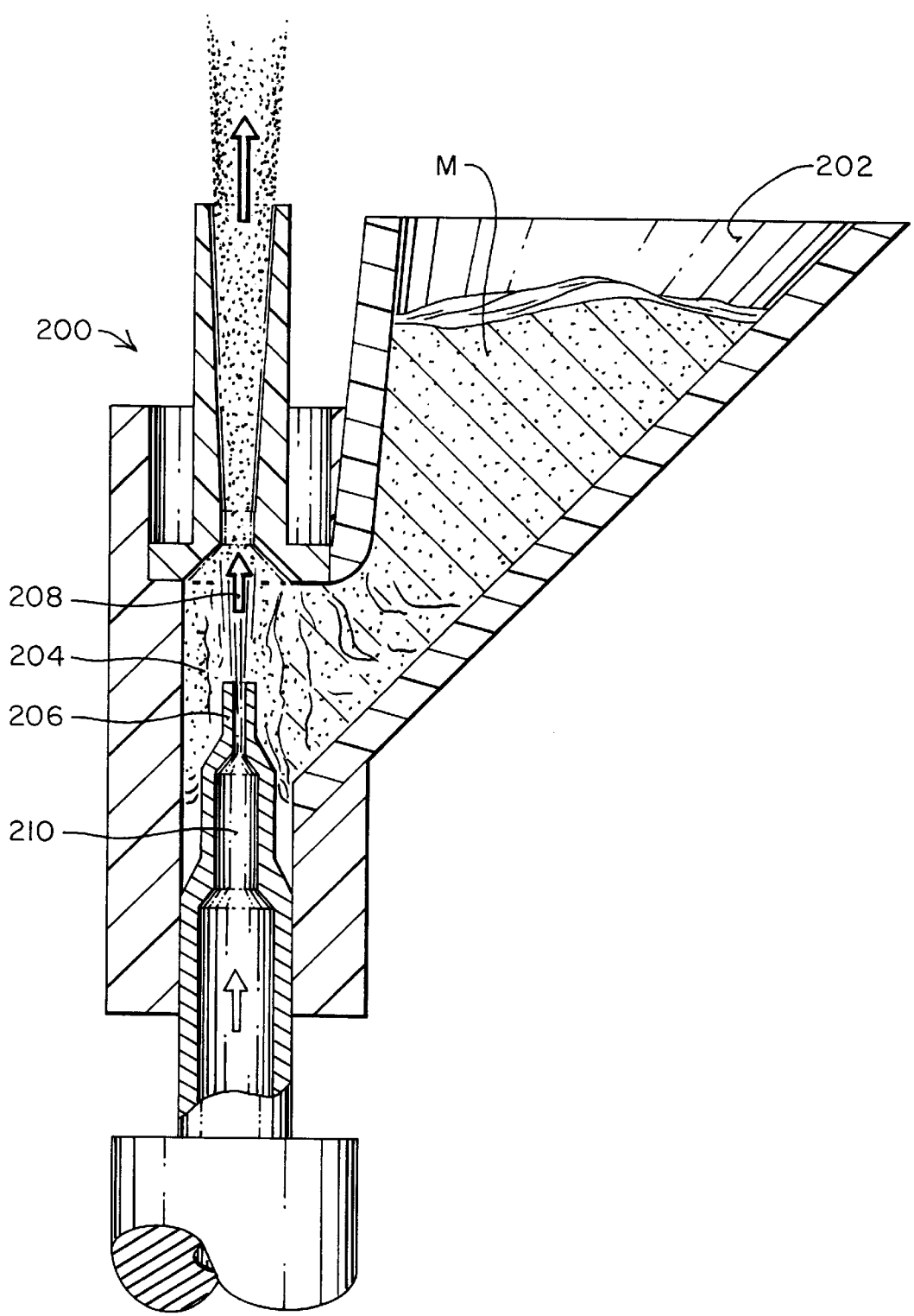

FIG_8
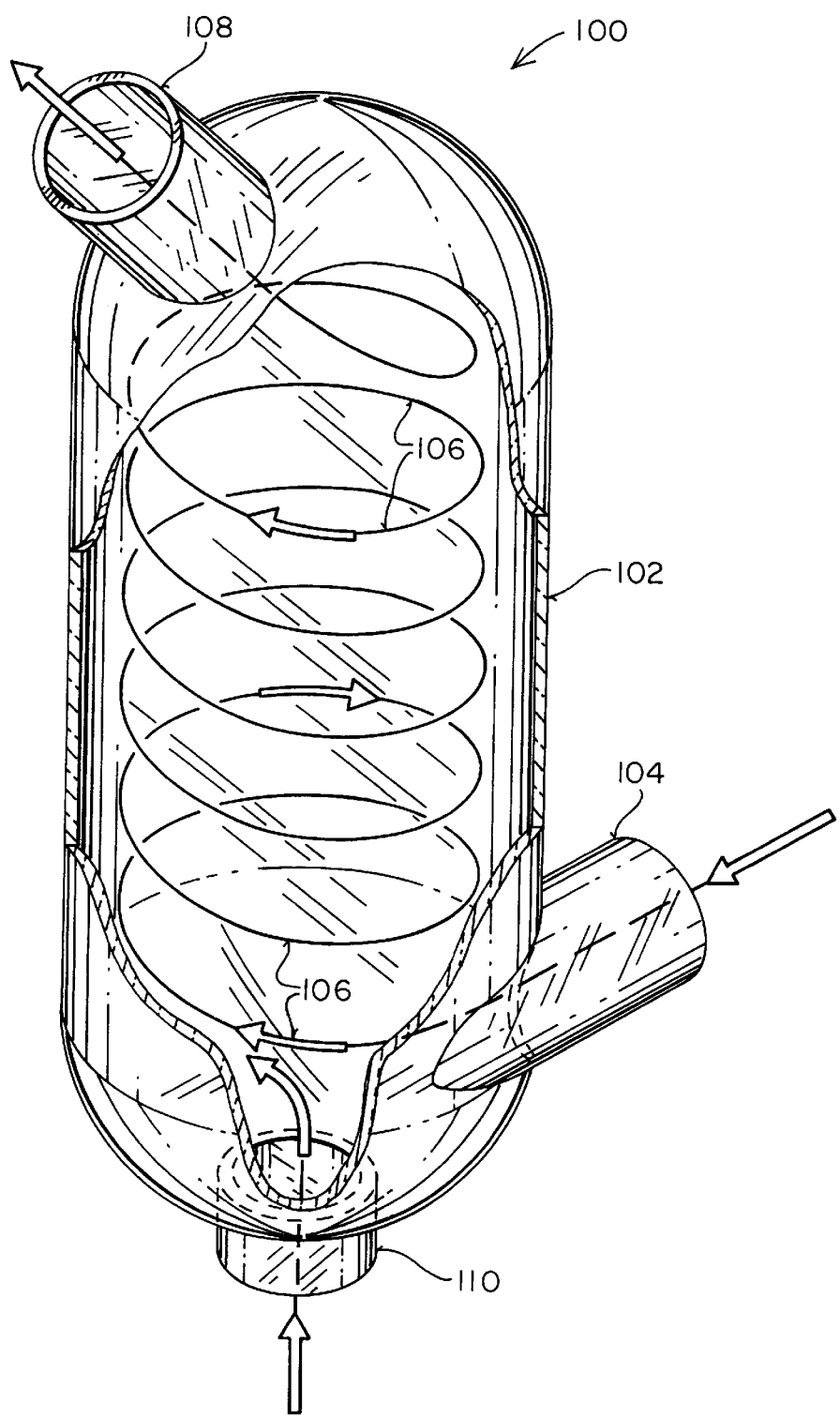

FIG_9
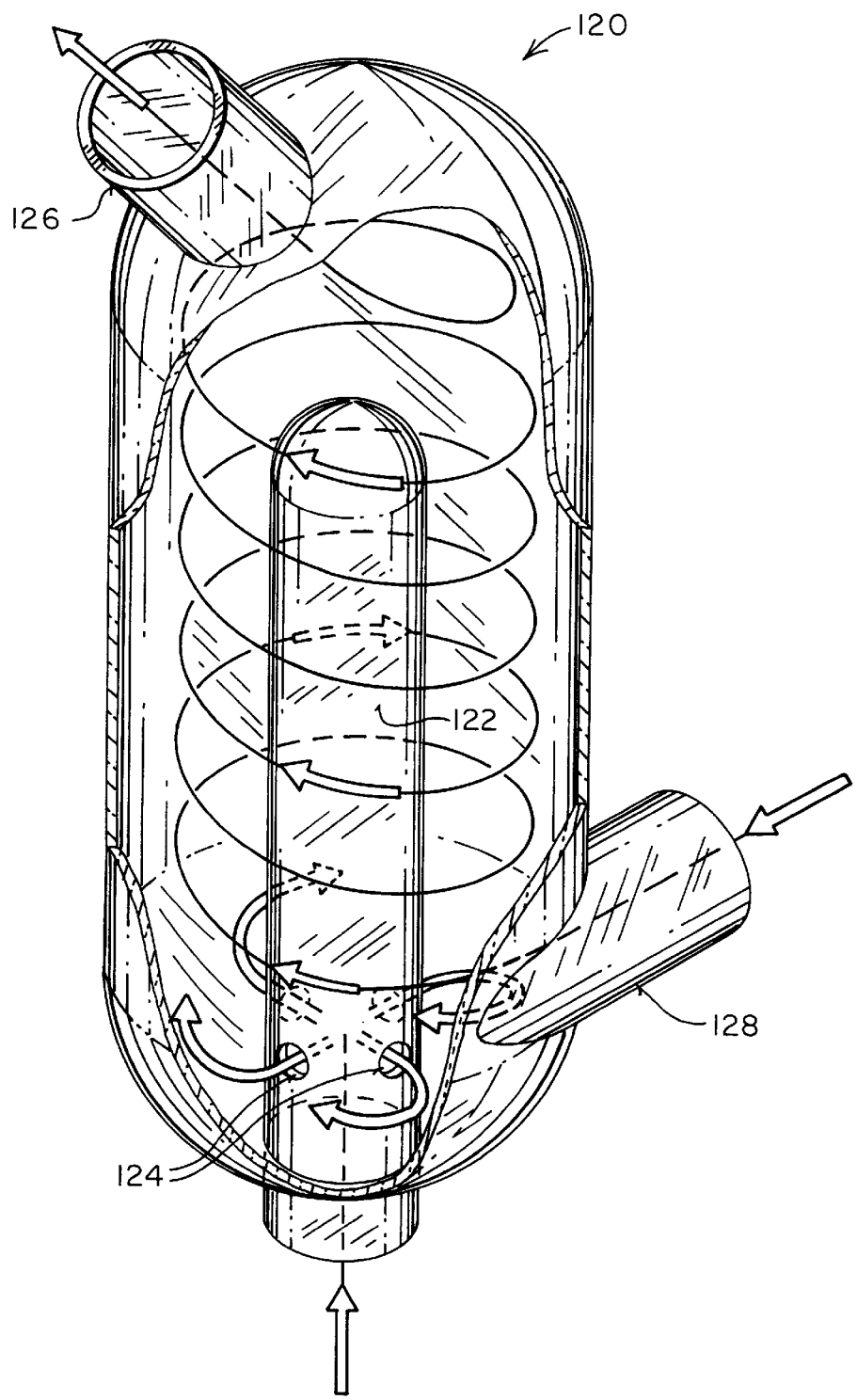

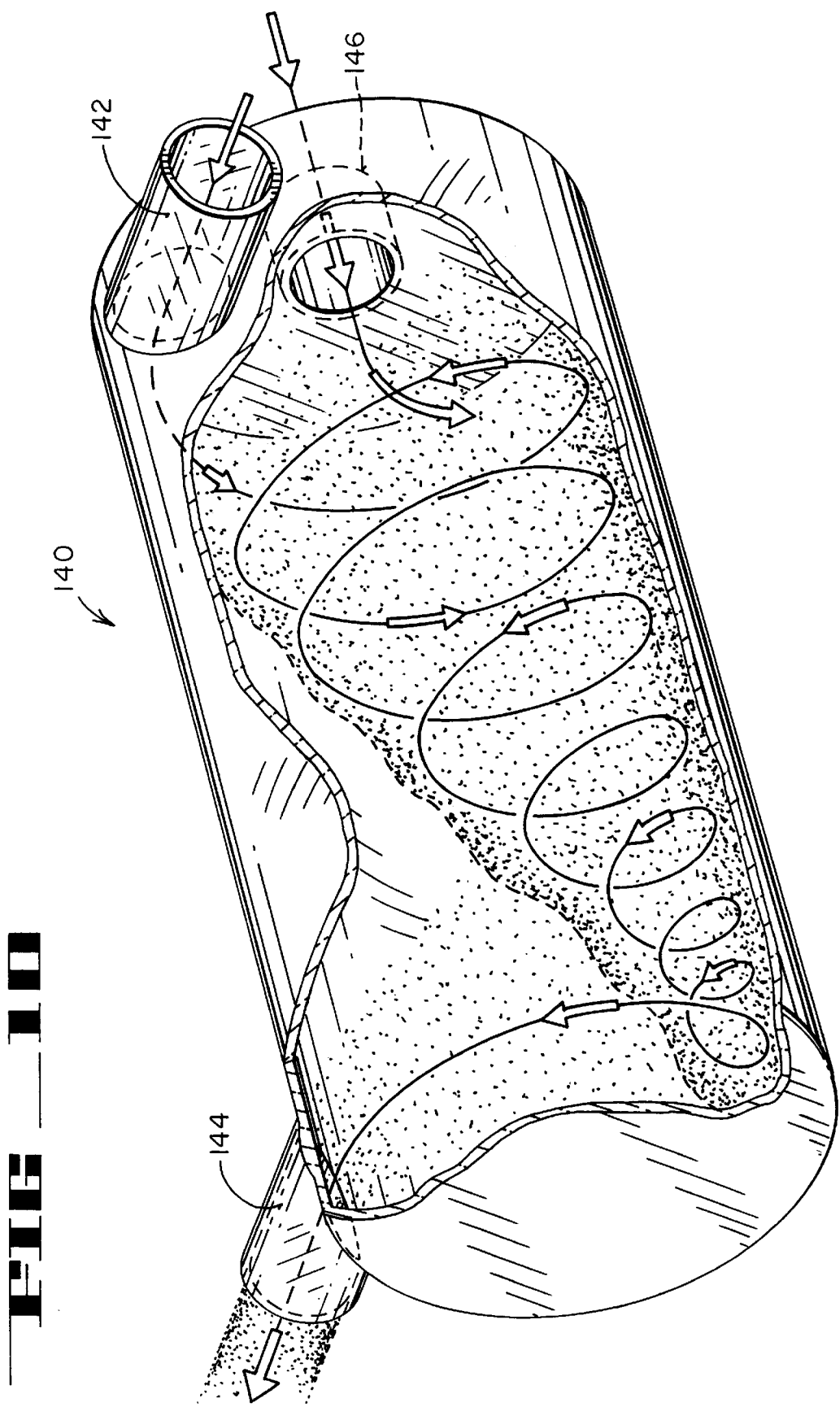
FIG_10

FIG _ 11A
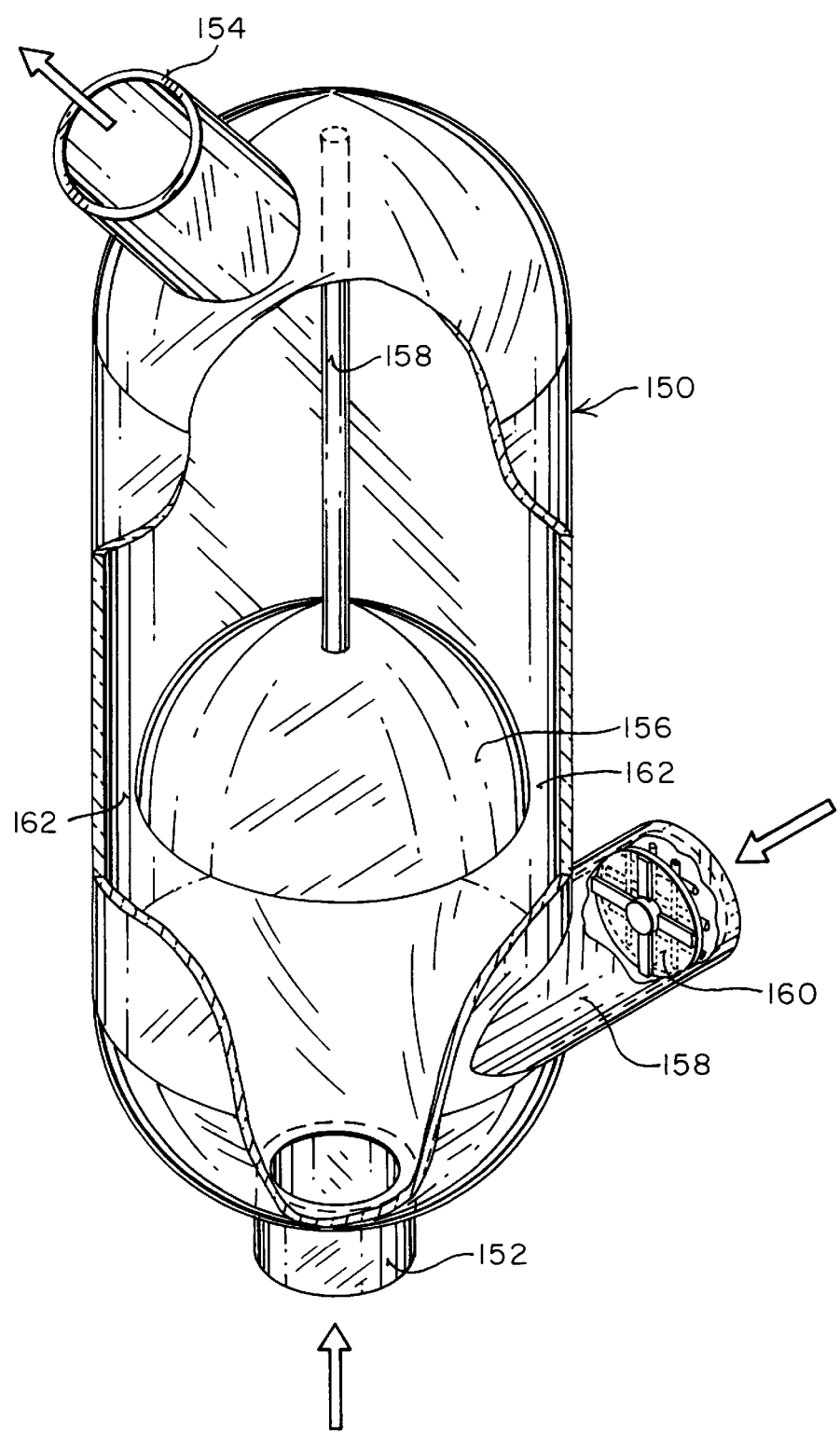

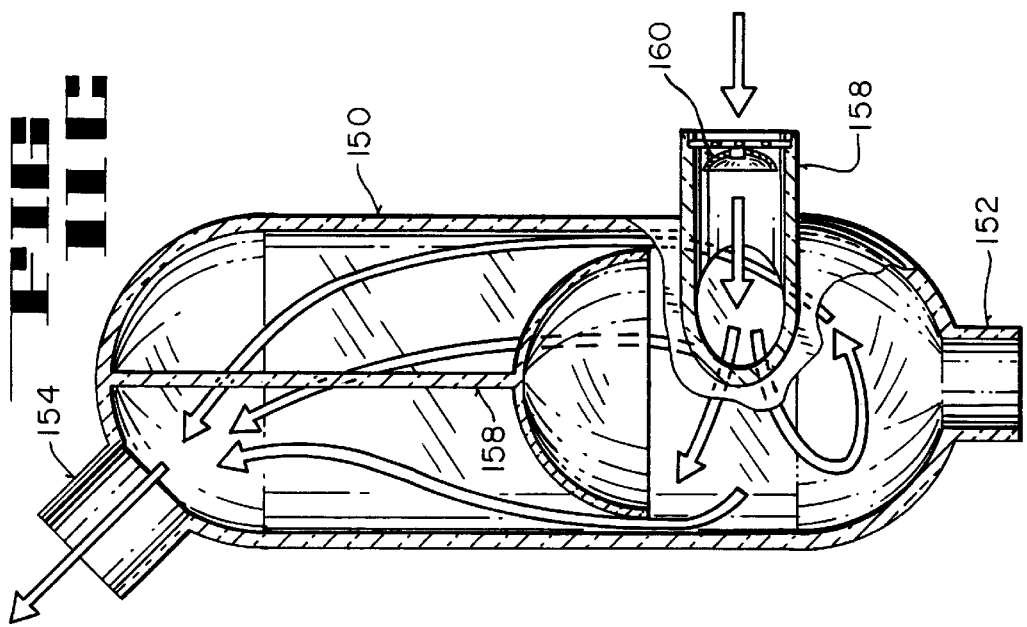
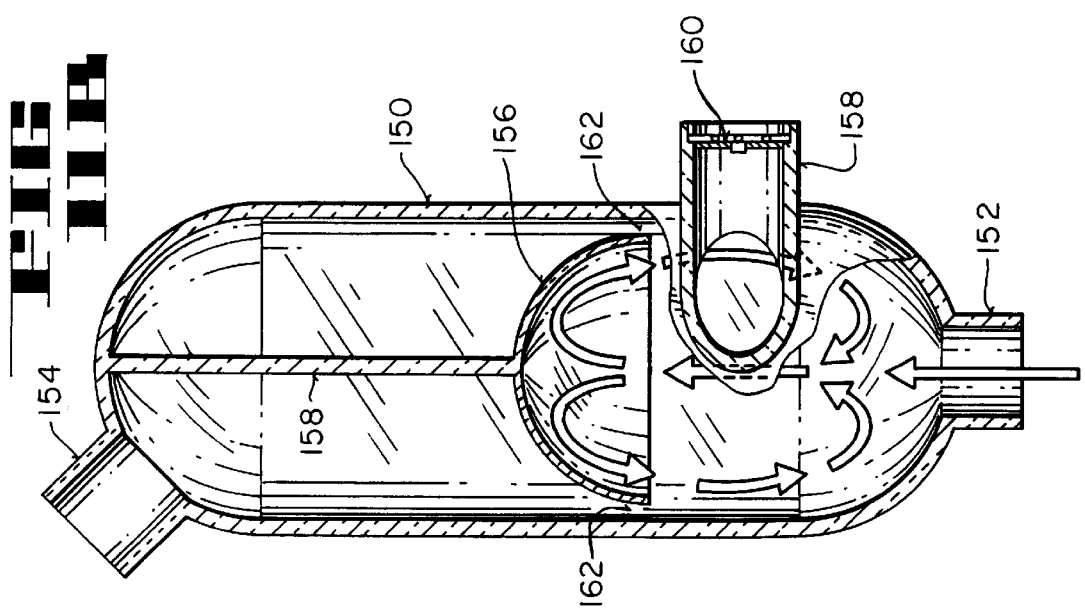

METHOD AND DEVICE FOR DELIVERING AEROSOLIZED MEDICAMENTS

This is a Continuation of application Ser. No. 08/576,885 filed Dec. 22, 1995, now U.S. Pat. No. 5,775,320, which is a continuation of Ser. No. 08/313,707 filed Sep. 27, 1994, now abandoned, which is a continuation of Ser. No. 07/910,048 filed Jul. 8, 1992, now U.S. Pat. No. 5,458,135, which is a continuation in part of Ser. No. 07/724,915 filed Jul. 2, 1991 (now abandoned), the disclosures of which is incorporated by reference.

BACKGROUND OF THE INVENTION

1. Field of the Invention

This invention relates to a structure and method of administering precisely measured doses of a therapeutic by inhalation.

An accurate mechanism for delivering precise doses of aerosol drugs into the interior of human lungs has been an objective of many workers in the art. One of the most popular aerosol delivery devices is the propellent-driven metered dose inhaler (MDI), which releases a metered dose of medicine upon each actuation. Although these devices may be useful for many medicines, only a small variable percentage of the medicine is delivered to the lungs. The high linear speed with which the dosage leaves the device, coupled with incomplete evaporation of the propellants, causes much of the medicine to impact and stick to the back of the throat. This impacting and sticking creates a local concentration of drugs much of which is eventually swallowed. In the trade, this impact area is called a "hot spot" and can cause local immuno-suppression and the development of fungal infections with bronchosteriods. With broncodilators, for instance, the swallowed dose can contribute to unwanted systemic side effects such as tremor and tachycardia.

MDI's also require a degree of coordination between activation and inhalation. Many patients are incapable of this task, especially infants, small children and the elderly. In an effort to overcome some of the above limitations of MDI's, others have interposed "spacers" between the conventional MDI and the patient. The primary function of these spacers is to provide extra volume to allow time for increased propellent droplet evaporation prior to inhalation and to reduce the velocity and impact of the medicine at the back of the throat. Although spacers do compensate for some of the inadequacies in the conventional MDI, it has been found that much of the medicine that may have ordinarily been deposited on the throat remains in the spacer and the total dose deposited in the lungs is small. It has been found that only approximately 8% of the medicine reaches the interior of the lung with conventional MDI's. Approximately 13% of the medicine reaches the lung when it is equipped with a spacer.

Other workers in the art have attempted to provide a metered dose of a medicant by using dry powder inhalers (DPI). Such devices normally rely on a burst of inspired air that is drawn through the unit. However, these units are disadvantaged in that the force of inspiration varies considerably from person to person. Some patients are unable to generate sufficient flow to activate the unit. DPI's have many of the disadvantages of MDI's in that a large percentage of the medicant is deposited in the throat because of incomplete particle dispersion and the impact at the rear of the throat. Although pocket size MDI's and DPI's are very convenient they have disadvantages some of which are cited above.

Other workers in the art have refined aqueous nebulization delivery systems. Although such systems require a continuous gas compressor, making them less portable than the MDI's and the DPI's, many nebulizers provide a low velocity aerosol which can be slowly and deeply inhaled into the lungs. Precision of dosage delivery, however, remains a serious problem and it is difficult to determine how much medicament the patient has received. Most nebulizers operate continuously during inhalation and exhalation. Dosage is dependent on the number and duration of each breath. In addition to breath frequency and duration, the flow rate, i.e., the strength of the breath that is taken from a nebulizer can effect the particle size of the dose inhaled. The patient's inhalation acts as a vacuum pump that reduces the pressure in the nebulizer. A strong breath can draw larger unwanted particles of medicant out of the nebulizer. A weak breath, on the other hand, will draw insufficient medicant from the nebulizer.

Electro-mechanical ventilators and devices have also been used in recent years to deliver inhalable materials to a patient. These devices permit mixing of a nebulized medicant into breathing circuit air only during pre-set periods of a breathing cycle. An example of this type of machine is the system taught by Edgar et al., in their U.S. Pat. No. 4,677,975, issued in July of 1987 where a nebulizer is connected to a chamber which in turn is connected to a mouthpiece, an exhaust valve, and an inlet valve. A breath detector and timer are used to deliver nebulized materials to the patient during a portion of the breathing cycle. However, in Edgar and others of this type, the patient's intake strength can effect the nebulizer operation with many of the consequences heretofore mentioned. Moreover, the amount of nebulized material delivered in each breath can vary significantly, contributing to inaccurate total dosages. In a modification of Edgar et al. (Elliott, et al. (1987) Australian Paediatr, J. 23:293–297), filling of the chamber with aerosol is timed to occur during the exhalation phase of the breathing cycle so that the patient is not inhaling through the device during nebulization. This design, however, requires that the patient maintain a constantly rhythmic breathing pattern into and out of the device, which is inconvenient and can contaminate the device with oval microbes. Moreover, no provision is made on the devices to efficiently capture the aerosol in the chamber so that as many as 80 breaths or more must be taken to obtain a dose of medication.

The delivery of therapeutic proteins and polypeptides by inhalation presents additional problems. Many protein drugs are produced recombinantly and can thus be very expensive. It is therefore important that loss of a protein drug within the delivery device be reduced or preferably eliminated. That is, substantially all drug initially charged within the device should be aerosolized and delivered to the patient without loss within the device or released externally of the device. The protein drugs should further be delivered to the patient under conditions which permit their maximum utilization. In particular, protein drugs should be completely dispersed into small particles in the preferred 1 $\mu$m to 5 $\mu$m size range which is preferentially delivered to the alveolar region of the lungs. The amount of protein drug delivered to the patient in each breath must also be precisely measured so that the total dosage of drug can be accurately controlled. Finally, it will be desirable to permit the delivery of highly concentrated aerosols of the protein drug so that the number of breaths required for a given dosage can be reduced, thus increasing accuracy and reducing the total time required for administration.

2. Description of the Background Art

U.S. Pat. Nos. 4,926,852 and 4,790,305 describe a type of "spacer" for use with a metered dose inhaler. The spacer defines a large cylindrical volume which receives an axially directed burst of drug from a propellant-driven drug supply. U.S. Pat. No. 5,027,806, is an improvement over the '852 and '305 patents, having a conical holding chamber which receives an axial burst of drug. U.S. Pat. No. 4,624,251, describes a nebulizer connected to a mixing chamber to permit a continuous recycling of gas through the nebulizer. U.S. Pat. No. 4,677,975, is described above. European patent application 347,779 describes an expandable spacer for a metered dose inhaler having a one-way valve on the mouthpiece. WO 90/07351 describes a dry powder oral inhaler having a pressurized gas source (a piston pump) which draws a measured amount of powder into a venturi arrangement.

SUMMARY OF THE INVENTION

The present invention provides methods and apparatus for producing an aerosolized dose of a medicament for subsequent inhalation by a patient. The method comprises first dispersing a preselected amount of the medicament in a predetermined volume of gas, usually air. The dispersion may be formed from a liquid, for example by injecting an air stream through a liquid reservoir of the drug, or from a dry powder, for example by drawing the powder into a flowing air stream from a reservoir using a venturi or other dispersion nozzle. The present invention relies on flowing substantially the entire aerosolized dose into a chamber which is initially filled with air and open through a mouthpiece to the ambient. The aerosolized dose of medicament flows into the chamber under conditions which result in efficient displacement of the air with the aerosolized material. By "efficient displacement," it is meant that at least 40% by weight of the aerosolized material entering the chamber will remain aerosolized and suspended within the chamber, thus being available for subsequent inhalation through the mouthpiece. It is further meant that very little or none of the aerosolized material will escape from the chamber prior to inhalation by the patient. Efficient displacement of air and filling of the chamber can be achieved by proper design of the chamber, as discussed below.

After the aerosolized medicament has been transferred to the chamber, the patient will inhale the entire dose in a single breath. Usually, the total volume of aerosolized medicament and air within the chamber will be substantially less than an average patient's inspiratory capacity, typically being about 100 ml to 750 ml. In this way, the patient can first inhale the entire amount of drug present in the dose and continue in the same breath to take in air from the ambient which passes through the chamber and which helps drive the medicament further down into the alveolar region of the lungs. Conveniently, the steps of aerosolizing the medicament, filling the chamber, and inhalation of the chamber contents may be repeated as many times as necessary to provide a desired total dosage of the medicament for the patient.

Apparatus according to the present invention comprise both a dispersion device for aerosolizing the medicament, either from a liquid or dry powder formulation of the medicament, and a chamber having an air inlet and patient mouthpiece for receiving the aerosolized medicament from the dispersion device. The chamber is designed and connected to the dispersion device in such a way that the aerosolized medicament will flow into the chamber and efficiently displace the internal air volume, as described above. The volume of the chamber will be at least as large as the maximum expected volume of aerosolized medicament to be transferred from the dispersion device. Usually, the chamber volume will be greater than the aerosol volume in order to reduce losses through the mouthpiece, with exemplary chamber volumes being in the range from 100 ml to 750 ml, as described above. The volume of aerosolized medicament will usually be in the range from 50 ml to 750 ml when the dispersion device is a liquid nebulizer and from 10 ml to 200 ml when the dispersion device is a dry powder disperser, as described in more detail below. In order to enhance efficient filling, the chamber will preferably define an internal flow path so that the entering aerosolized medicament will follow the path and displace air within the chamber without substantial loss of the medicament through the mouthpiece. Alternatively, the chamber may include a baffle which acts to entrap a high velocity aerosol, particularly those associated with dry powder dispersions.

In a preferred aspect, the chamber is generally cylindrical and is connected to the dispersion device by a tangentially disposed aerosol inlet port located at one end of the cylinder. The mouthpiece is then located at the opposite end of the cylinder, and aerosolized medicament flowing into the chamber will follow a generally vortical flow path defined by the internal will of the chamber. By also providing an ambient air inlet at the same end of the cylindrical chamber, the patient can first inhale the medicament and thereafter breath in substantial amounts of ambient air, thus sweeping the interior of the chamber to efficiently remove substantially all aerosolized medicament present and help drive the medicament further into the patient's lungs.

In further preferred aspects, the ambient air inlet of the chamber will be protected, typically through a one-way valve structure which permits air inflow but blocks aerosol outflow, so that aerosol will not be lost as it enters the chamber. The chamber may also comprise vortical baffles, typically in the form of an axially aligned tube or conical cylinder within the interior of the chamber, to restrict dispersion of the aerosol within the chamber and improve delivery efficiency.

In an alternate preferred aspect, the chamber is generally cylindrical with an axially oriented aerosol inlet port located at one end. The mouthpiece is located at the other end of the cylinder, and an internal baffle is located between the aerosol inlet and the mouthpiece to prevent direct passage of the aerosol to the mouthpiece (which could result in loss of medicament well before the chamber has been efficiently filled). The internal baffle is preferably hemispherical in shape with a concave surface oriented toward the aerosol inlet. Such a construction has been found particularly useful in initially containing dry powder dispersions which are often introduced using a high velocity (frequently sonic) gas stream. The chamber further includes a tangential ambient air inlet port disposed in the chamber wall between the aerosol inlet and the internal baffle. By inhaling through the mouthpiece, the patient is able to establish a vortical flow of ambient air which will sweep the contained aerosol past the baffle and through the mouthpiece.

In yet another aspect of the present invention, the apparatus for producing aerosolized doses of a medicament comprises the dispersing device, means for delivering pressurized gas to the dispersing device, the aerosol chamber, and a controller capable of selectively controlling the amount of pressurized air delivered to the dispersing device in order to produce the desired single doses of medicament and deliver said doses to the chamber. The controller may include means for timing the actuation of a compressor or means for controlling the amount of gas released from a pressurized cylinder, as well as a mechanism for counting and displaying the number of doses delivered from the chamber during a particular period of use. Still further, the controller may include a microprocessor and a keypad for inputting information to the microprocessor.

In exemplary devices, the controller may comprise a timer connected to selectively actuate a valve, such as a solenoid valve, on a gas cylinder. Alternatively, the timer may turn on and off an air compressor to regulate the amount of air delivered to the dispersing device. In portable and hand-held apparatus, the controller may simply be a release button or mechanism that actuates a spring or air driven piston to deliver a specific amount of gas. The controller could also be a metered valve which could release a fixed amount of liquid propellant to the dispersing device (in a manner similar to a metered dose inhaler).

The method and the apparatus of the present invention are particularly effective for delivering high value drugs, such as polypeptides and proteins, to a patient with minimal loss of the drug in the device. Moreover, the method and device provide for a very accurate measurement and delivery of the doses, while employing relatively simple and reliable equipment. Further advantages of the present invention include the ability to vary the total dosage delivered, either by controlling the number of breaths taken or by controlling the amount of medicament in each breath. Still further, the method and device of the present invention permit the delivery of relatively concentrated doses of the medicament in order to reduce the amount of time and number of breaths required for the delivery of a total dosage of the medicament, particularly when using dry powder medicament formulations.

BRIEF DESCRIPTION OF THE DRAWINGS

FIG. 7 illustrates a venturi nozzle which may be used for dispersing dry powder medicament formulations when used in systems constructed in accordance with the principles of the present invention;

FIGS. 8–11 illustrate various exemplary chambers which may be used in the aerosol delivery systems of the present invention.

DESCRIPTION OF THE SPECIFIC EMBODIMENTS

Figure 1:
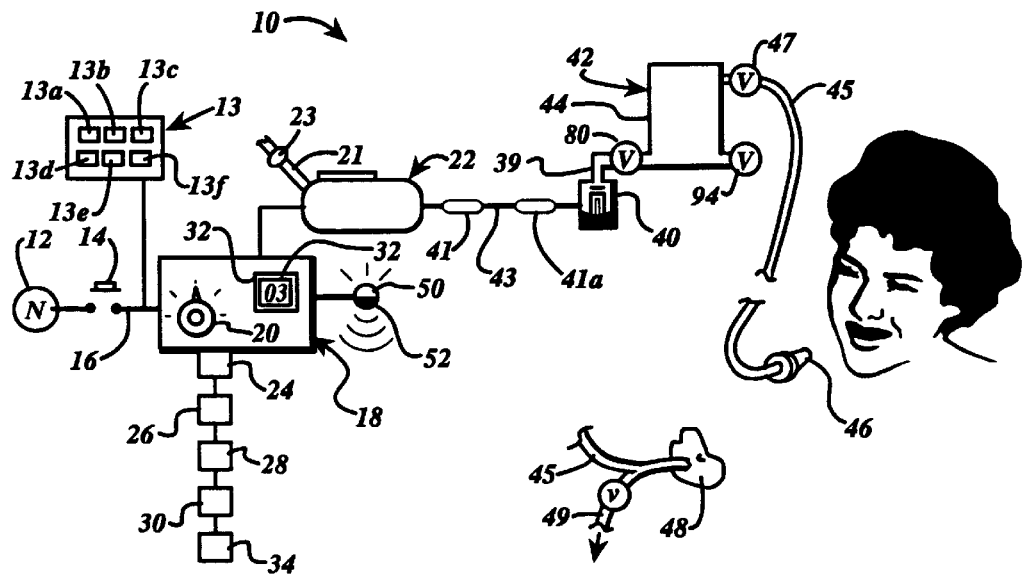
FIG. 1 is a schematic-diagrammatic view of the invention.

The method and device of the present invention are useful for delivering a wide variety of medicaments, drugs, biologically active substances, and the like, to a patient's lung, particularly for systemic delivery of the medicament or the like. The present invention is particularly useful for delivering high value medicaments and drugs, such as proteins and polypeptides, where efficient delivery and minimum loss are of great concern.

The apparatus of the present invention will usually comprise the following basic components: a means for producing a metered volume of gas, a mixing chamber for generating an aerosol bolus from either a liquid or a powder, a reservoir that contains the medicament, and a holding chamber that efficiently captures the aerosol bolus to maintain the aerosolized particles in suspension and allow a patient to inhale the aerosol by a slow, deep inspiration, thereby effectively distributing the aerosolized medicament to the distal region of the lungs.

A gas source will usually deliver a preselected volume of gas at greater than about 15 psig in order to produce a sonic velocity jet in an aerosol producing region (although sonic velocity is not always necessary). The pressurized gas is required to efficiently atomize the liquid or break apart the powder producing an aerosol having particles that are predominantly 1 to 5 µm in diameter. In addition, the volume of the gas bolus must be less than a fraction of a patient's inspiratory volume, preferably between 100 to 750 ml. Suitable gas sources include:

1) an air compressor with a timer to control the operating period of the compressor (where the timer comprises at least a portion of the controller discussed hereinafter);

2) a compressed gas cylinder with a solenoid valve controlled by a timer;

3) a liquid propellant with a metering valve and an evaporation chamber;

4) a spring piston pump; and 5) a pneumatic pump.

The means for producing the aerosol will usually consist of a constricted orifice that produces a high velocity gas flow to atomize a liquid or break apart powder agglomerates. The present invention is designed to be used with a conventional jet nebulizer that operate with airflow rates in the range from 3 to 13 L/min at about 15 psig, with the flow rate depending largely on the nozzle geometry of the nebulizer. The present invention further provides a means of controlling the volume of air delivered to the nebulizer in order to produce an aerosol bolus having a specific volume that can be contained in the aerosol holding chamber. By controlling the gas source to deliver a specific volume of gas, the system can employ a variety of nebulizers available from commercial vendors, such as Marquest, Hudson, Baxter, and Puritan Bennett.

The present invention can also operate with a powder jet disperser as a means of generating an aerosol. A pressurized gas jet produces a highly turbulent gas flow that serves to break apart powder agglomerates producing an aerosol having single particles of the preformed powder. An example of a suitable powder/gas mixing chamber is a simple nozzle with a venturi ejector, as shown in FIG. 7. An advantage of this type of powder mixer is that the gas flow through the nozzle is only a fraction of the entrained airflow through the venturi. This reduces the air capacity so that the required volume of gas for dispersing the powder could be delivered from a small "pocket-sized" gas source.

In addition, the powder dispersing apparatus must produce a pressure pulse having a long enough duration (typically 0.01 to 1 second) to adequately fluidize the powder and efficiently dispense the powder from the reservoir. A small diameter nozzle, less than 0.020 inch is acceptable and less than 0.015 inch is preferable, in order to achieve an acceptable duration of the pressure pulse at peak pressures exceeding 15 psig with a volume of gas that is small enough to be contained in a small holding chamber.

Referring now to the drawings wherein like numerals indicate like parts, the numeral 10 generally indicates an exemplary apparatus constructed in accordance with the principles of this invention. The apparatus is powered by an electrical source 12 that provides energy for a controller, typically in the form of a microprocessor 18. The present invention, however, does not require the use of an electrical or digital controller, so long as some means is provided for supplying preselected gas volumes for aerosol bolus.

The microprocessor 18 is a general purpose microcontroller unit (MCU) such as that sold by Motorola under their Model Number 68HC05. This unit has on-chip peripheral capabilities and the on-board memory system 30. The on-chip peripheral capability of the Motorola unit includes multiple input ports, one of which receives the input data from the keypad 13 via line 16. The microprocessor 18 has a plurality of output ports and its functioning will be more fully understood as the components of the invention are described.

Keypad 13 has six input keys that are important to performance, namely; 13a,13b, 13c, 13d, 13e, and 13f. The volume or amount of each aerosolized dose is selected by controlling the length of time a compressor 22 is turned on by pressing the "puff size" button 13a. The keypad 12 is programmed so that a first press of button 13a will display a choice of puff sizes on an LCD 32. Additional pressings of the button will select the desired size. A "puff counter actuator" button 13b is pressed which will cause the LCD 32 display "00". A second press of 13b energizes the air compressor 22 via output line 38 for a 13a. This produces the first aerosolized dose or bolus of a medicament for inhalation. The LCD display 32 will change from 00 to 01 and the LCD will increase by one upon each additional activation of the compressor. The patient will continue activating puffs with button 13b until the prescribed number of puffs have been taken. As these puff events are occurring, the time and number are stored in memory 30.

To view a record of previous uses of the device, a dosage recall button 13c is pressed which causes LCD 32 to display prior dates, time, puff sizes and number of puff formation events. Successive pressings of the button 13c will enable scrolling of the patient's dosage history. Reversal of scroll direction is accomplished by pressing button 13d and then continuing to scroll with 13c. The button 13e is a clock/calendar button. Pressing the button 13e causes the LCD 32 to display the current date and time. After the device is used and a series of puffs have been taken, the system will automatically default five minutes after the last puff to display the actual time and date on the LCD display. Thus, the device is a clock/calendar when not in actual use and during the use and date or time can be view by pressing 13e.

Air from compressor 22 is communicated to a mixer 40. The mixer 40 may be a nebulizer, a dry powder dispenser or other type of nebulizer known to the prior art. When unit 40 is a dry powder dispenser, the compressed air from compressor 22 may optionally be first subjected to coalescing filter 41 and a desiccant filter 41a. When unit 40 is a nebulizer, a particle filter 21 may optionally be placed at the intake 23 of the compressor to filter out articles before the air is compressed. In either case, the medicament or drug will preferably be in the form of a small particulate, usually having a aerodynamic size in the range from 1 μm to 5 μm. It is known that particles in this size range are most efficiently delivered to the alveolar regions of the lungs.

An exemplary dry powder venturi nozzle 200 is illustrated in FIG. 7. The venturi nozzle 200 includes a side port 202 which receives an initial charge of powder medicament M, typically a lyophilized protein or polypeptide. The powder is drawn into dispersion chamber 204 at the point where nozzle orifice 206 introduces a high velocity gas stream in the direction of arrow 208. The high velocity gas stream will result from pressurized gas or air in plenum 210, which may be provided by a separate air compressor 22 (FIG. 1) or an air or gas cylinder (not illustrated). The low pressure caused by the air or gas stream will draw the powder continuously into the dispersion chamber 204 where agglomerates of the powder are broken into smaller sizes within the preferred 1 μm to 5 μm range by the turbulent shear effect in the chamber.

In any event, unit 40 is of a type that will nebulize or mix a defined amount of medicant with the preselected amount of compressed air received from compressor 22. This defined amount, referred to as a dosage or bolus, flows into a chamber 42 via the conduit 39. The chamber 42 is transparent, typically having a glass, transparent plastic, or similar wall 44.

A critical aspect of the present invention is the ability to transfer the aerosolized medicament from the mixer 40 into the chamber 42 without substantial loss of medicament through the mouthpiece or within the chamber. Such losses will be minimized so that at least about 40% by weight of the medicament delivered to the chamber will remain aerosolized and suspended within the chamber after the entire volume has been transferred. Preferably, at least about 55% will remain suspended, more preferable at least about 70%. Such low losses are desirable since the total amount of drug which may be introduced into the chamber for each transfer is maximized, and thus the amount which may be inhaled in each breath by a patient is increased. Additionally, even small losses of high valued drugs, such as proteins and polypeptides, can become significant over time. Still further, the ability to deliver a concentrated aerosol dispersion of drug into the chamber will increase the concentration of drug delivered to the patient with each breath. Such high concentration dosages are preferable since they can reduce the total number of breaths necessary to deliver a prescribed amount of drug, thus increasing the total amount of time required for the treatment.

Loss of aerosolized medicament can be reduced by minimizing mixing between the aerosolized medicament and the displaced air as the chamber is being filled. Minimum mixing between the aerosol transferred from the mixing chamber 40 and the displaced air within chamber 42 can be enhanced by properly designing the chamber 42 as well as the inlet flow geometry of the aerosol into the chamber. Particularly preferred geometries are illustrated in FIGS. 2–5 and 8–11, as described in more detail hereinbelow.

A light 50 and/or an audible signal 52 will alert the user that a puff is ready to be withdrawn from chamber 42 when the compressor 22 shuts down. At this point in time, the aerosolized bolus of medicine is quite visible. From the holding chamber 42 the medicament is inhaled by the patient via a conduit 45 through a mouthpiece 46 or in the case of small children or infants, a face mask 48. A one-way check valve 47 is disposed across conduit 45 to prevent exhalation into chamber 42. The signals 50 and 52 are set to begin immediately after operation of the compressor 22 ceases. The cessation of the compressor sound will also alert the patient that bolus formation is complete. This sequence is repeated for each bolus and the microprocessor 18 will count and record each instance of compressor activation so that the prescribed number of aerosolized boluses have been administered. The number of boluses, their hour and date and their size (time f compressor use), are recorded, stored and recallable at a future time for display on LCD 32 by pressing dosage history button 13c.

Figure 2:
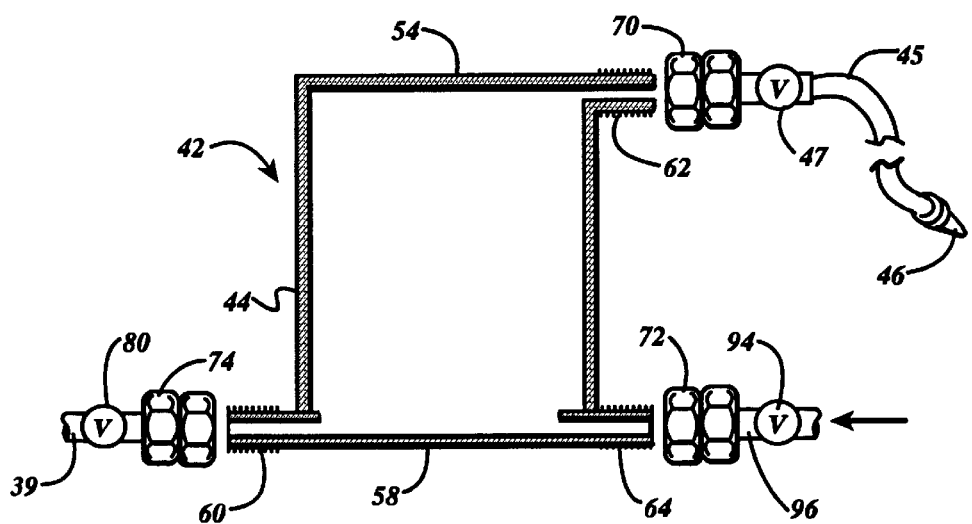
FIG. 2 is a diagrammatic cross-sectional view of a holding chamber.
Figure 3:
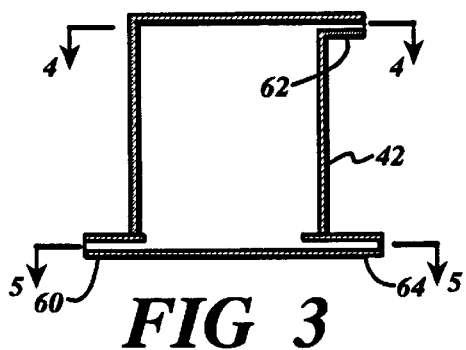
FIG. 3 is a diagrammatic view of the holding chamber.
Figures 4, 5:
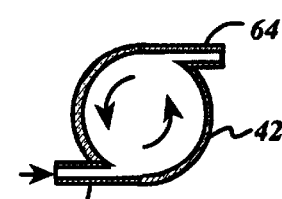
FIG. 4 is a cross-section along the line 4—4 of FIG. 3.
FIG. 5 is a cross-section along the line 5—5 of FIG. 3.

One embodiment of the aerosol holding chamber 42 is best seen in cross-section in FIG. 2. The chamber 42 is comprised basically of a top 54, the previously mentioned transparent sidewall 44 and a bottom 58. The chamber 42 is equipped with an aerosol intake stub fitting 60 at the lower portion thereof. The chamber top is equipped with an inhalation stub 62. Also at the bottom 58 is an atmospheric intake stub 64. The stubs are formed to accept conventional connector fittings 70, 72 and 74 respectively. The fittings connect the conduits 45, 96 and 80 to the stub-fillings 60, 62 and 64. The fittings permit the ready interchange of chambers having different volumetric capacities.

Disposed in a conduit 39, between unit 40 and chamber 42, is a valve 80 that is opened before use of the device and closed between uses. The valve 80 serves as a vapor lock to prevent evaporation of fluid from unit 40 when the nebulizer is not in use. Valve 80 can be controlled by hand like a stop-clock, or it may be electronically controlled by the MCU 18 so that upon pressing the puff counter/actuator button 13b, valve 80 opens and then closes by default if the machine is not used for a set period. Disposed across inhale line 45 is a one-way check valve 47. A one-way check valve 94 is also disposed across the air intake conduit 96.

Particularly preferred chamber geometries are illustrated in FIGS. 8–11. Chamber 100 in FIG. 8 comprises a cylindrical body 102 with a tangential aerosol inlet port 104. The tangential aerosol inlet port 104 will be connected to a suitable aerosol dispersing device, usually either a nebulizer or a dry powder device (as described above), preferably a nebulizer, and the aerosol will enter and assume a vortical flow pattern, as indicated by arrows 106. The entry of the aerosol will displace air initially present in the chamber 100 through mouthpiece 108. Usually, but not necessarily, the chamber 100 will be oriented vertically with the mouthpiece at the top. After the entire aerosol bolus has entered the chamber 100 (typically only partially filling the chamber leaving a "buffer" of air near the mouthpiece 108), the patient will inhale through the mouthpiece 108, drawing in ambient air through ambient air inlet 110, thus sweeping the chamber of the aerosolized medicament. Ambient air inlet 100 will usually have a one-way valve, such as a flap or diaphragm valve (not illustrated) in order to prevent loss of aerosol as the aerosol is introduced through port 104.

Chamber 120 in FIG. 9 is similar to chamber 100, except that an inlet tube 122 extends into the chamber interior, forming a vortical baffle. Apertures 124 are disposed about the inlet tube 122 to permit entry of air as the patient inhales through mouthpiece 126. Ambient air inlet 128 is similar to inlet 104 in FIG. 8.

A horizontally disposed chamber 140 is illustrated in FIG. 10. Chamber 140 includes both a tangential aerosol inlet 142 and tangential mouthpiece 144. Thus, aerosolized medicament will enter through the inlet 142 and move horizontally across the chamber interior toward the mouthpiece 144. An advantage of this design is that the aerosol particles will tend to drop below the level of the mouthpiece 144 as they cross the chamber. Thus, loss of the medicament through the mouthpiece 144 will be minimized. Ambient air inlet 146 is provided to permit air infusion as the patient inhales through the mouthpiece 144.

a preferred chamber 150 for use with dry powder dispersion devices, such a venturi nozzle 200 in FIG. 7, is illustrated in FIG. 11A. The chamber 150 will generally be maintained with its axis oriented vertically, with an aerosol inlet 152 at its lower end and a mouthpiece 154 at its upper end. The chamber 150 further includes an internal baffle 156 which is suspended from a rod 158 attached to the upper end of the chamber. The baffle 156 is preferably hemispherical, with its open or concave end oriented downwardly toward aerosol inlet 152. The purpose of the baffle 156 is to contain the initial plume of aerosol created by the high velocity air or gas stream. The hemispherical design is preferred since it will redirect the initial flow of aerosol back downward, creating a recirculation as indicated by the arrows in FIG. 11B. Other geometries for the baffle, including flat plates, perforated plates, cylinders, cones, and the like, might also find use, with the primary requirement being that the baffle design be able to provide an initial containment zone within the chamber.

After an aerosolized dose or bolus of medicament has been introduced to the chamber 150, the patient will inhale through the mouthpiece 154, drawing ambient air in through ambient air inlet 158. The inlet 158 includes a one-way flap or diaphragm valve 160 which permits the inflow of air but prevents the initial loss of medicament as the aerosolized dose enters through the inlet 152. The ambient air inlet 158 is disposed tangentially on the chamber 150, and entry of ambient air through the inlet cause a vortical (as illustrated in FIG. 11C) which will cause the suspended medicament particles to move radically outward (due to the induced cyclone effect) and be carried upward by the airflow through the annular region 162 between the periphery of the baffle 156 and the interior wall of the chamber 150.

Surprisingly, the design of chamber 150 has been found to be able to receive a volume of aerosolized medicament greater than the chamber volume without substantial loss of medicament through the mouthpiece. It is believe that the baffle 156 can act as a "concentrator," which contains the medicament particles in the region below the baffle while permitting air flow through the annular region 162. Such concentration is achieved while still maintaining the aerosolized particles in suspension and with the ability to subsequently transfer the medicament particles to the mouthpiece by introducing a vortical flow of ambient air through inlet 158, as described above.

Figure 6A:
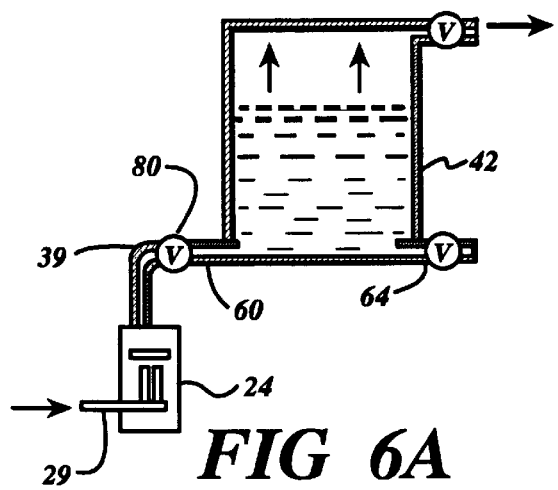
FIG. 6A–6D are diagrammatic views disclosing the stages of operation.
Figure 6B:
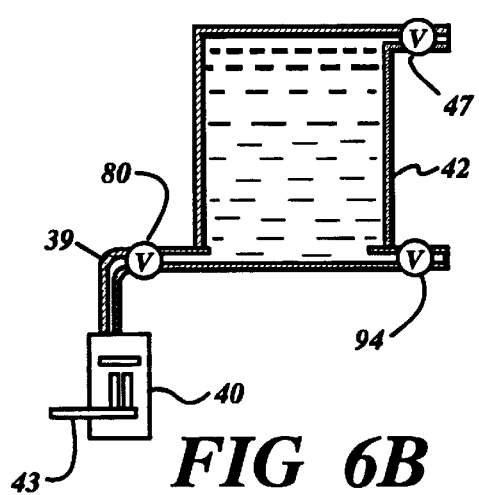
Figure 6C:
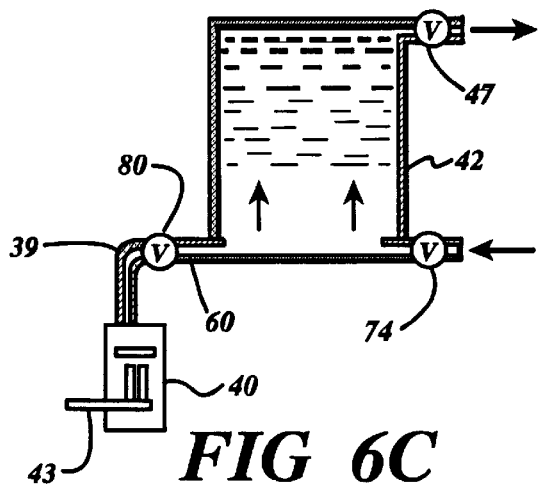
Figure 6D:
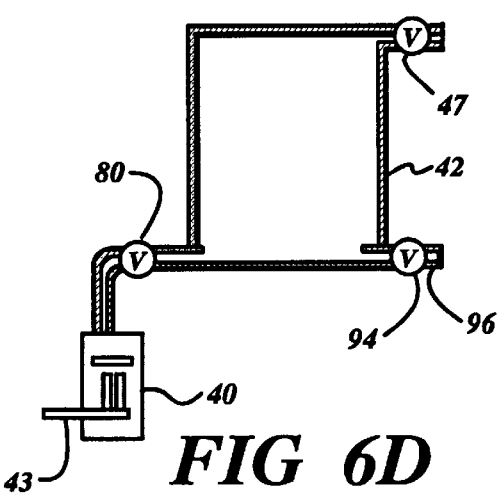

In operation, the patient or medical attendant will ready the device by operating the puff size button 13a. Button 13b is pressed a second time to energize compressor 22 and a pre-selected amount of air under a constant pressure is delivered to unit 40 for mixing or nebulizing to form the first puff. The medicament begins filling the chamber 42 from the bottom (FIG. 6A) through valve 80 and stub fitting 60 and a cloudy, observable "puff" is formed as seen in FIG. 6B. During this time interval, valve 94 is closed.

After the vessel or chamber 42 is filled, the signals 50 and 52 are activated for several seconds by the timer function of the microprocessor 18. The duration of both signals will be present in the control program 24. As a breath is taken, valves 47 and 94 will open to permit the puff to enter the lungs and to permit additional atmospheric air to enter the chamber from the bottom through conduit 96.

The volumetric size of chamber 42 is only a fraction of the capacity of the patients' lungs usually being from 200 ml to 1000 ml, typically being about 500 ml. Inhalation by the patient will thus initially draw the entire dose of medicament into the lungs. The volume of aerosol transferred to the chamber will typically be about 10 ml to 750 ml, and the air that enters through valve 94 can thus act as an air piston to drive the smaller volume of aerosol deep into the user's lungs. The bottom to top filling and vertical flow pattern result in a minimum of dispersion and dilution of the aerosol. Moreover, the sweeping of chamber 50 with air after each inhalation helps assure substantially complete delivery of the drug to the patient.

The atmospheric or pure air and the medicament bolus, each moves from the chamber 42 through the one-way check valve 47 into the patient's mouth via the conduit 45. A mask 48 with a one-way exhalation port is used for patients that require same. A one-way valve 47 may be used to prevent the patient from accidentally exhaling into the chamber 42.

FIG. 6A–6D show illustrations of the sequence of bolus generation and withdrawal from the aerosol holding chamber 42.

The following examples are offered by way of illustration, not by way of limitation.

EXPERIMENTAL

Experimental Equipment

Air supply—a nitrogen cylinder with a regulator, a needle valve, a pressure gauge, and a solenoid valve that is operated with a timer with a resolution of 0.01 second.

Jet Nebulizer—Rapid-Flo™, (Allersearch, Vermont Victoria, Australia).

Powder Disperser—A venturi (as illustrated in FIG. 7) having a 0.013 inch diameter jet nozzle.

Aerosol Holding Chambers—Fabricated from plastic with internal volumes of 750 ml. Design 1—3-inch cylindrical chamber with spherical top and bottom and one 90°—port at the base, one 45°—port at the top and one tangential port on the side (as illustrated in FIG. 8). Design 2—3-inch cylindrical chamber with spherical top and bottom and a 1 inch cylindrical spacer located axially along the center of the chamber. Three ports—one 90°—port at the base, one 45°—port at the top and one tangential port on the side (as illustrated in FIG. 9). Design 3—3-inch cylindrical chamber with spherical top and bottom; a 2-½ inch hemispherical baffle held in the center of the chamber with a rod. The baffle was located approximately 2 inches above the base of the chamber. Three ports—aerosol intake: 90°—port at the base, mouthpiece: 45°—port at the top and makeup air intake: tangential port on the side (as illustrated in FIG. 11). Design 4—3-inch cylindrical chamber with spherical top and bottom; a 2-½ inch hemispherical baffle located 2-¾ inches above the base on a cone (as illustrated in FIG. 11).

Methods

The four aerosol chamber designs were tested using either the jet nebulizer or the powder dispenser. Design 1 was tested using either the 90°—port at the base for the aerosol intake or the tangential port as the aerosol intake.

The total airflow through the apparatus, the aerosol generator and the holding chamber, was measured with a rotameter connected to the mouthpiece of the holding chamber. The flow was set to the desired rate with the needle valve. The pressure was maintained above 15 psig to ensure sonic velocity in the nozzle of the aerosol generator.

Once the airflow was set, the sample was loaded into the aerosol generator. The operating period was set on the timer. A toggle switch on the timer opened the solenoid valve sending air through the aerosol generator and producing the aerosol. We observed the distribution of the aerosol in the holding chamber and could observe when the aerosol began to flow out of the chamber. The maximum length of time that the aerosol generator could be operated and still capture all of the aerosol in the holding chamber was determined by adjusting the operating period on the timer and repeating the steps listed above. The aerosol dose volume was calculated from the flow rate and the time the solenoid was open. A vacuum line was connected to the holding chamber following an actuation to clear the chamber of the aerosol before actuating again.

A 0.9% saline solution was used in testing the different holding chamber configurations with a Rapid-Flo™ nebulizer. The nebulizer was operated at flow rate of 19 L/min which resulted in 24 psig across the jet of the nebulizer.

The powder disperser was tested at a pressure of 30 psig which resulted in a flow rate of 10.4 L/min through the apparatus. Approximately 5 mg of a test powder, prepared by spray drying a solution of mannitol and bovine serum albumin, was loaded into the venturi intake and the solenoid valve was actuated. We checked for powder remaining in the venturi intake to determine whether there was an adequate air supply to disperse the powder. The particle size distribution measured from the chamber using an Aerosizer (API, Hadley, Mass.) particle size analyzer showed that the aerosol contained particles between 1 and 4 $\mu$m in diameter.

Results

Results comparing the different chamber designs for containing the aerosol are reported in Table 1. The maximum volume of the aerosol contained by the chamber was calculated from the maximum operating time and the total airflow. The proportion of the aerosol volume to the volume of the chamber given in the % Chamber Volume column is a way of comparing the effectiveness of the different chamber designs for containing the aerosol. The air volume needed to disperse 5 mg of powder could be efficiently captured in all of the chamber configurations tested. The designs that induced a vertical airflow patern in the chamber retained a larger volume of aerosol.

TABLE 1

Aerosol Capture Efficiency for several Holding Chamber Designs

| Chamber | Nebulizer | | | Powder Disperser | | |
|---|---|---|---|---|---|---|
| | Aerosol Volume | % of Chamber Volume | Increase over base | Aerosol Volume | % of Chamber Volume | Increase over base |
| Design 1 bottom fill | 348 mL | 45.8% | — | 69. mL | 9.24% | — |
| Design 1 tangential fill | 665 mL | 88.7% | 1.94 | 95.3 mL | 12.7% | 1.38 |
| Design 2 center baffle | 728 mL | 97.1% | 2.12 | 104 mL | 13.9% | 1.50 |
| Design 3 hemisphere baffle | 950 mL | 127% | 2.77 | 164 mL | 21.9% | 2.37 |
| Design 4 | 855 mL | 114% | 2.49 | 161 mL | 21.5% | 2.33 |

Conclusions

An aerosol holding chamber can be designed that efficiently captures a measured volume of aerosol. A chamber designed to induce vortical airflow pattern in the chamber by a tangential aerosol intake or using baffles distributes the aerosol more evenly in the chamber without loss from the mouthpiece. For use with a nebulizer, a vortical airflow produces a higher concentration of medicament in the chamber so that an effective dose could be taken with fewer puffs. The results with the powder disperser show that the vortical flow and properly designed baffles are effective in containing a powder aerosol produced by a turbulent jet.

It should be understood that the preferred embodiments of the present invention have been disclosed by way of example and that other modifications may occur to those skilled in the art without departing from the scope and spirit of the appended claims.

What is claimed is:

1. An apparatus for producing aerosolized doses of a medicament, said apparatus comprising:
    a reservoir that contains a pre-selected amount of a medicament;
    means for aerosolizing the preselected amount of medicament using pressurized gas to produce a flow of aerosolized medicament;
    means for delivering pressurized gas to the aerosolizing means;
    a chamber having an air inlet and a mouthpiece and being connected to receive and temporarily hold the entire flow of aerosolized medicament from the aerosolizing means for subsequent delivery to a patient, wherein gas present in the chamber will be displaced by the aerosolized medicament; and
    a controller including means for selectively controlling the amount of pressurized gas delivered to the aerosolizing means, whereby delivery of single doses of medicament to the chamber may be effected.

2. An apparatus as in claim 1, wherein the controller includes means for timing actuation of the pressurized gas delivering means.

3. An apparatus as in claim 1, wherein the controller includes means for counting and displaying the number of doses delivered to the chamber.

4. An apparatus as in claim 1, wherein the controller includes a microprocessor and a keypad for inputting information to the microprocessor.

5. A hand-held, portable apparatus for producing an aerosolized dose of a medicament for delivery to a patient, said apparatus comprising:
    a reservoir that contains a preselected amount of a medicament;
    a preselected amount of aerosol-generating material for producing an aerosolized dose of said medicament;
    a controller for delivering the preselected amount of aerosol generating material to an aerosol generator to withdraw substantially the entire amount of the medicament from the reservoir and form the aerosolized dose of medicament; and
    an actuator for activating the controller to deliver the aerosol-generating material to the aerosol generator to produce the aerosolized dose of medicament having an aerodynamic size in the range from 1 to 5 microns wherein said aerosolized dose may be withdrawn from the apparatus by a patient using a slow deep inspiration.

6. The apparatus of claim 5, wherein the aerosol generating material is selected from the group consisting of compressed air, compressed gas, and liquid propellants.

7. The apparatus of claim 5, wherein actuation of the aerosol generating material is timed to adequately aerosolize the dose of medicament.

8. The apparatus of claim 5, wherein the controller includes a counter and display for counting and displaying the number of doses delivered to the chamber.

9. The apparatus of claim 5, wherein the controller includes a microprocessor and a keypad for inputting information to the microprocessor.

10. The apparatus of claim 9, wherein the keypad is programmed to display a choice of dose sizes of the aerosolized medicament on an LCD.

* * * * *